United States Patent [19]

Landgraf et al.

[11] 4,278,907
[45] Jul. 14, 1981

[54] D.C. SUBFRACTIONAL HORSEPOWER MOTOR WITH FLUX SHUNT FOR VARIABLE RPM ADJUSTMENT

[75] Inventors: Hermann Landgraf, Heppenheim; Juergen Wohlgemuth, Darmstadt, both of Fed. Rep. of Germany

[73] Assignee: Siemens Aktiengesellschaft, Berlin & Munich, Fed. Rep. of Germany

[21] Appl. No.: 59,295

[22] Filed: Jul. 20, 1979

[30] Foreign Application Priority Data

Aug. 3, 1978 [DE] Fed. Rep. of Germany ....... 2834099

[51] Int. Cl.³ .......................... H02K 1/00; H02K 23/40
[52] U.S. Cl. ...................................... 310/191; 310/47; 310/154
[58] Field of Search .............. 310/154, 40 R, 40 MM, 310/47, 50, 190, 191, 209, 254; 318/360, 538, 539; 433/52, 84, 98, 99, 103, 114, 125, 126, 132, 142

[56] References Cited

U.S. PATENT DOCUMENTS

| 501,532 | 7/1893 | Offrell | 310/190 |
| 1,377,229 | 5/1921 | Tanner | 310/190 |
| 1,399,803 | 12/1921 | Schafer | 310/154 X |
| 1,470,092 | 10/1923 | Modigliani | 310/154 |
| 2,949,552 | 8/1960 | Benoit | 310/191 X |
| 3,209,457 | 10/1965 | Billin et al. | |
| 3,842,300 | 10/1974 | Daykin et al. | 310/154 X |
| 4,110,649 | 8/1978 | Mas | 310/191 |

FOREIGN PATENT DOCUMENTS 45433 9/1934 France .
995691 6/1965 United Kingdom .

Primary Examiner—Mark O. Budd
Attorney, Agent, or Firm—Hill, Van Santen, Steadman, Chiara & Simpson

[57] ABSTRACT

For adjusting the rpm with the assistance of mechanical regulators consisting of low-retentivity magnetic material, the air gap between the rotor and the stator, and/or the magnetic return between the stator field poles of opposite polarity, and/or a magnetic shunt is adjusted. The illustrative embodiments are particularly provided for d.c. subfractional horsepower motors for the drive of dental tools.

10 Claims, 14 Drawing Figures

D.C. SUBFRACTIONAL HORSEPOWER MOTOR WITH FLUX SHUNT FOR VARIABLE RPM ADJUSTMENT

CROSS REFERENCE TO RELATED APPLICATION

Reference is hereby made to a continuation in part application continuing the disclosure of the present application and seeking generic coverage for certain developments based on the present disclosure.

BACKGROUND OF THE INVENTION

The invention relates to a d.c. subfractional horsepower motor with preferably permanent magnet excitation and variable rpm adjustment, particularly for the drive of dental tools.

In d.c. subfractional horsepower motors it is usual to change the rpm via electrical elements. A change of the rpm is known either through the change of the armature voltage or (in motors with stator windings) by changing the magnetic flux with the assistance of resistance elements.

In d.c. subfractional horsepower motors with permanent magnet excitation and normal construction (with cylindrical rotor), an rpm change or control exclusively by means of changing the armature voltage is known. In dental technology, for example, where one employs such motors for the drive of drilling, grinding, or cutting tools, such motors are operated over an rpm range of approximately 4,000 through 40,000 rpm given a rated voltage of approximately 24 volts. A change of the rpm ensues from a foot switch via a changeable resistance.

It is often desirable to increase the extant rpm range either toward an upper speed range or toward a lower speed range. This is not satisfactorily possible solely by changing the armature voltage, because, for example, in the lower rpm range a power output that is too small, or a torque that is too small would be supplied at the motor drive shaft. Up to now, an expanded rpm range without undue power losses, or without excessive torque losses could only be achieved, essentially, with the assistance of a change of mechanical gear ratio. In dental technology, for example, in order to be able to expand the aforementioned rpm range of the motor of approximately 4,000 through 40,000 rpm up to about 120,000 rpm and down to approximately 800 through 1,000 rpm a suitable handpiece with reduction or translation gears is placed on the drive motor.

However, gears in and of themselves and particularly given such small dimensions and relatively high rpms as for example in the said dental handpiece drives represent wearing parts which are particularly in need of maintenance. Moreover, they require a relatively large fabrication outlay; because of the relatively small space available for housing a gear in such subfractional horsepower motors and, particularly, in those for driving dental handpieces, especially high demands are made with respect to material and observation of the fits of the gear parts. A further disadvantage is to be seen in the frequent change of the handpieces which is required when the dentist must work with different rpm ranges during the treatment of a patient.

SUMMARY OF THE INVENTION

The object of the invention is to create an improvement and simplification with respect to the above. To this end, a d.c. subfractional horsepower motor is to be created in which the rpm or the rpm range can be changed while largely retaining the power output and retaining the previous adjustability of the rpm (by means of changing the armature voltage).

This object is inventively achieved in a d.c. subfractional horsepower motor of the type initially cited in that, for adjusting the rpm with the assistance of mechanical regulators consisting of low-retentivity magnetic material, the air gap between rotor and stator and/or the magnetic return are changed and/or a magnetic shunt is adjusted. What is meant by low-retentivity magnetic material is a material which exhibits a high saturation, a low coercive field strength (coercivity) and a high permeability such as, for example, soft iron.

Advantageous further developments and embodiments of the invention are disclosed in the subclaims.

Particular advantages can be achieved in a d.c. subfractional horsepower motor with permanent magnet excitation and in the employment of such a motor in dental technology for the drive of dental handpieces because the basic set of hand and angle pieces with different gear gradations can thereby be significantly reduced.

A number of exemplary embodiments of the invention are explained in greater detail on the basis of the accompanying sheets of drawings; and other objects, features and advantages will be apparent from this detailed disclosure and from the appended claims.

DETAILED DESCRIPTION

Figure 1:
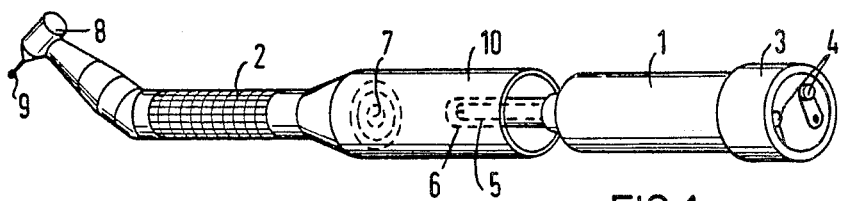
FIG. 1 shows a drive motor for the drive of a dental hand and angle piece in schematic representation.

FIG. 1 shows a drive motor 1 for a dental hand and angle piece 2 in a diagrammatic representation. The drive motor 1, an electric d.c. motor with permanent magnet excitation, is supplied with electric energy via a supply cable (not illustrated) secured to the back end 3 of the motor, contact elements 4 being provided for the transmission of electric current from the supply cable to the motor.

A protective sleeve 6 surrounding the drive shaft 5 of the motor projects from the front end of the motor housing When the handpiece 2 is placed on the drive motor 1, the drive shaft 5 engages with a drive shaft 7 of the handpiece 2, which drive shaft 7 drives a tool 9 (for example a drill) rotatably mounted in the head part 8.

10 designates a sleeve of low-retentivity magnetic material, annulus-shaped in cross section, and secured to the handpiece 2, which sleeve 10, when the drive motor 1 is coupled to the handpiece by engagement of shafts 5 and 7, encloses the motor up to the back end 3. By means of slipping the sleeve 10 over the drive motor 1, the magnetic flux is changed—as a result of the increase in cross section and/or the addition of material of higher permeability to the soft-iron return path—whereby the rpm range normally attainable without this by means of changing the armature voltage can be additionally changed over a specific range (toward the lower speed values).

Figure 2:
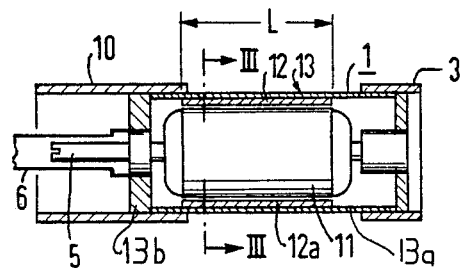
FIGS. 2, 3 and 4 show the basic construction of the drive motor according to FIG. 1 in longitudinal and cross section, FIG. 3 being taken generally as indicated at III—III in FIG. 2.
Figure 9:
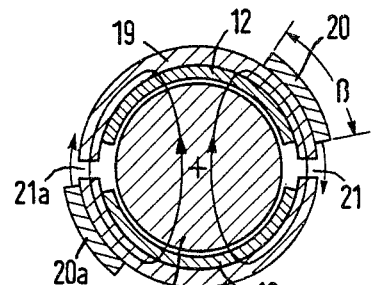
FIGS. 7, 8 and 9 and 10 show further exemplary embodiments of the inventive motor in cross section.
Figure 10:
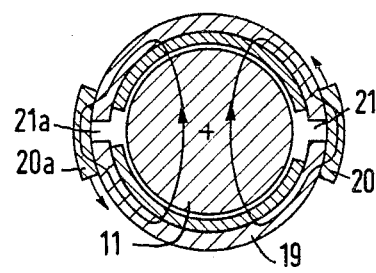
Figure 7:
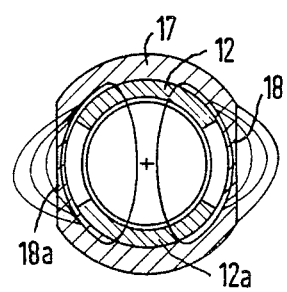

FIG. 2 shows the motor 1 with the sleeve 10 partially slipped on in a basic illustration. In the illustration, the rotor or armature of the motor is referenced with 11, two permanent magnets with length L located diametrically opposite one another are referenced with 12, 12a, and the motor housing accepting the permanent magnets is referenced with 13, which parts together make up the stator of the motor. With the permanent magnets 12, 12a being magnetized as shown in FIGS. 9 and 10, the housing 13 which consists of low-retentivity magnetic material represents the magnetic return path for the stator magnets both at its annular casing 13a in the area of the permanent magnets as well as at the front face of the motor (i.e. at annular front wall 13b). The return formed in this manner is a stationary return, in contrast to the sleeve 10 which can be slipped on casing 13a and is likewise of a magnetic material with low-retentivity properties, which represents a return whose position can be changed (e.g. by making sleeve 10 removable to leave casing 13 as the only magnetic return path, sleeve 10 being replaced by a nonmagnetic sleeve in FIG. 1 for operation over a higher rpm range, for example). The thickness of the wall of the sleeve 10 which can be slipped over the casing 13a of the housing 13 is significantly thicker in comparison to the wall thickness of the casing 13a; given an assumed casing wall thickness of approximately 0.6 mm, the wall thickness of sleeve 10 amounts to approximately three or four times this casing wall thickness. All such materials which exhibit a demagnetization characteristic which is as flat as possible come under consideration as the permanent magnet material for the permanent magnets 12, 12a; advantageously however, cobalt samarium ($CoSm_5$) may be used.

Figure 3:
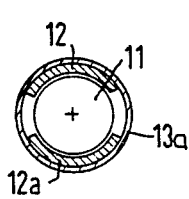
Figure 4:
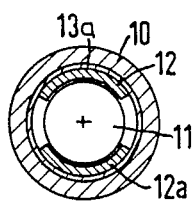

In FIGS. 3 and 4, which show the drive motor 1 in cross section (taken along the line III—III of FIG. 2), the drive motor is illustrated once without the sleeve 10 slipped on FIG. 3) and once with the sleeve 10 slipped on (FIG. 4). As will be explained in greater detail after the figure description, the magnetic flux can be changed by means of an associated sleeve of magnetic material (such as sleeve 10) both with respect to the magnetic flux of the armature as well as in view of the return path for the permanent magnet excitation magnetic flux. When the sleeve 10 is slipped on, the magnetic reluctance of the low retentivity "magnetically soft" magnetic material providing the return path between the pole ends of the permanent magnets 12, 12a is significantly smaller than without the sleeve. By means of increasing the magnetic flux, the rpm is reduced with respect to the normal rpm (when the sleeve is not slipped on) according to the relationship $n \sim (1/100)$. The reduction factor for an rpm range reduction amounts to approximately 0.5 depending on the thickness of the casing or shell 13a. The magnetic flux determining the rpm is limited by means of the attainment of magnetic saturation given a specific wall thickness of the sleeve 10 forming part of the return magnetic flux path.

The rpm range which can be selected by means of changing the magnetic flux allows the gear gradations to be dispensed with in the handpiece 2, whereby the handpiece 2 can be substantially more simply manufactured. Depending upon the rpm range for which they are required, the hand pieces need only be equipped either with or without the sleeve 10 of magnetic material. The sleeve 10 can also be removably mounted on the handpiece 2 or can also be a component part of the drive motor 1.

Figure 5:
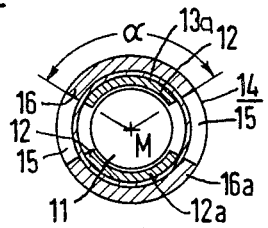
FIGS. 5 and 6 show a variant of the embodiment illustrated in FIGS. 3 and 4.
Figure 6:
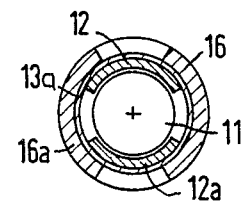

FIGS. 5 and 6 illustrate a variant to the embodiment illustrated in FIGS. 2 through 4. Instead of the sleeve 10 in FIG. 4 which has an annulus-shaped cross-section, a sleeve 14 with recesses 15 lying diametrically opposite one another is provided, which recesses leave two bar-like sections 16, 16a with segmental annulus-shaped or arcuate cross section and a circumferential angle $\alpha$ of approximately 120 degrees. The sections 16, 16a are connected with one another at the front face by means of bridges or the like consisting of, preferably, magnetically non-conductive (nonmagnetic) material. (The end walls such as 13b would also be nonmagnetic material in this embodiment.)

Figure 8:
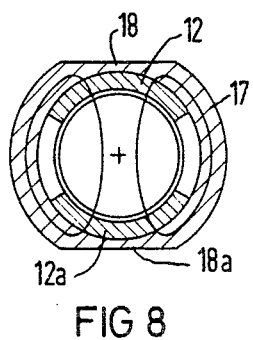
Figure 11:
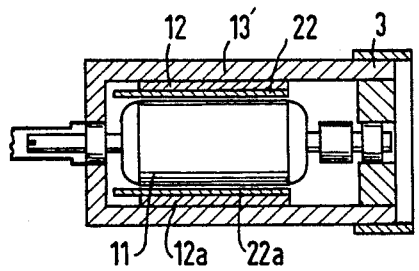
FIGS. 11, 12 and 13 show a further exemplary embodiment of the inventive motor in longitudinal and cross section.

The sleeve 14 with the two sections 16, 16a is arranged so as to be rotatable by 90 degrees with respect to the motor housing 13, so that the two sections 16, 16a can be brought into the position illustrated in FIG. 6 in which they respectively overlap the ends of the permanent magnets 12, 12a so that a good flux transfer from outwardly directed magnetic poles of the permanent magnets 12, 12a to the sections 16, 16a is given. In this position, a greater yoke cross section with lower magnetic reluctance and, thus, a better magnetic return is present in comparison to the position according to FIG. 5. (See the magnetic flux paths shown in FIGS. 8 and 10.) A reduced rpm of the motor again ensues in the position according to FIG. 6 corresponding to the relation $n \sim (1/\phi)$.

Two further variants of this principle are illustrated in the next figures, FIGS. 7 through 10. In the exemplary embodiment according to FIGS. 7 and 8, a yoke 17 consisting of low-retentivity magnetic material and rotatably seated e.g. inside of the motor housing is arranged around the two permanent magnets 12, 12a which yoke exhibits constricted cross section portions 18, 18a lying diametrically opposite one another. If the yoke is turned with respect to the permanent magnets 12, 12a so that the constricted cross section portions 18, 18a are situated between the pole ends of the magnets 12, 12a, then a reduced flux is to be registered here (at the location with the greatest flux density per se). The rpm of the motor, thus, is greater given this yoke adjustment (FIG. 7) than in the position shown in FIG. 8. The yoke 17 is here again to be used as a magnetic return whose location (e.g. angular position) can be changed.

In the exemplary embodiment according to FIGS. 9 and 10, the rpm is changed both by means of changing the effective length of the air gap in the magnetic flux path as well as by means of changing the magnetic return properties. A sleeve 19 of magnetic material is arranged around the permanent magnets 12, 12a, which sleeve represents a stationary return, in contrast to the two sections 20, 20a which are rotatably arranged with respect to the sleeve 19 and represent a return whose location can be changed. The two sections 20, 20a extend over a circumferential angle $\beta < 90$ degrees and can be pushed in the one position over recesses 21, 21a of the stationary return part 19 (FIG. 10). The recesses 21, 21a form an additional air gap between the pole ends of the magnets 12, 12a which is smallest in the position according to FIG. 10. In this position, the magnetic return accommodates the largest amount of flux and the rpm of the motor is at its lowest according to the relationship $n \sim (1/\phi)$.

In the exemplary embodiment according to FIGS. 11 through 14, an rpm change is achieved by means of an air gap change between stator and rotor as well as by adjustment of a magnetic shunt associated with the magnets.

The motor housing 13' in the exemplary embodiment according to FIG. 11 which again consists of low-retentivity magnetic material is relatively thick-walled, so that a stationary return which is relatively high per se but no leakage flux to the exterior of the housing 13' is present. The magnetic reluctance between the outer pole ends of the magnet and the housing 13' is likewise low. Two sections 22, 22a of low-retentivity magnetic material are arranged between the permanent magnets 12, 12a and the rotor 11, which sections, as can be seen from FIGS. 12 and 13, can be inserted between the stator 13 and the rotor 11; namely, in such manner that the effective air gap between the inner poles of the permanent magnets 12, 12a and the rotor 11 is changed. The sections 22, 22a essentially extend over the same angular range α as the permanent magnets 12, 12a.

In the initial position (FIG. 12), the air gap is relatively small and the armature 11 is permeated by the entire magnetic flux $\phi$. In the final position (FIG. 13), on the other hand, a relatively large air gap 23 is present between the rotor 11 and the permanent magnets 12, 12a and, thus, a greater magnetic reluctance; moreover, a part of the total magnetic flux is shorted via the pole shoes 22, 22a which are turned by 90 degrees with respect to the position according to FIG. 12. Thus, the magnetic flux in the armature is smaller in comparison to the position according to FIG. 12, and the rpm is correspondingly higher for the adjusted position of FIG. 13 according to the relationship $n \sim (1/\phi)$.

Figure 13:
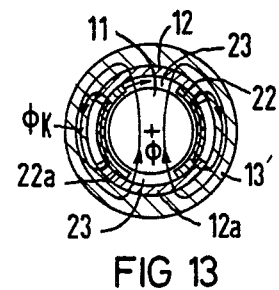
Figure 14:
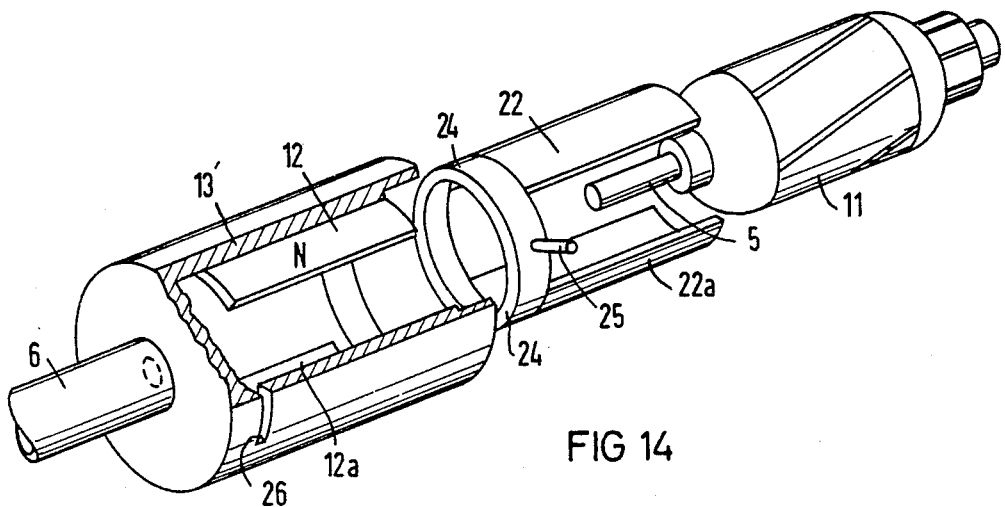
FIG. 14 is a diagrammatic illustration of the exemplary embodiment illustrated in principle in FIG. 11.

In FIG. 14, the exemplary embodiment schematically illustrated in FIGS. 11 through 13 is once again shown in diagrammatic representation, particularly in order to reveal the adjustment possibility for the sections 22, 22a. The two sections 22, 22a consisting of low-retentivity magnetic material are held by means of a ring 24 which, in order to prevent magnetic shorts, consists of a non-magnetic material. An actuation pin 25 projects radially from the ring 24, said actuation pin projecting radially through a guidance groove 26 arranged in the motor housing 13' over an angular range of 90 degrees. Thereby, an adjustment from the position shown in FIG. 12 into the position shown in FIG. 13 can easily be carried out, as needed, by hand from the exterior of housing 13'.

Three basic principles of an rpm change by means of magnetic flux change can be derived from the exemplary embodiments:

(1) Flux change by means of changing the cross section in the soft-iron return (FIGS. 1 through 8).

(2) Flux change by means of air gap change (FIGS. 9 through 13), (3) Flux change by means of magnetic shunt (FIGS. 11 through 14), whereby as can be seen for example from the illustrated exemplary embodiments, a combination of a number of the three principles is also possible. In the exemplary embodiment illustrated last, an adjustable pole shoe is present which, on the one hand, serves for bridging the air gap in the position according to FIG. 12 and, on the other hand, shunts parts of the magnets in the position according to FIG. 13.

In the solutions according to (1), one first proceeds from the condition that the cross sections of armature and the return path are dimensioned in such manner that the magnetic induction in the armature ($B_A$) and the return ($B_R$) lie below the saturation induction of the low-retentivity magnetic material (e.g. 10 in FIG. 4; 16, 16a in FIG. 6; 17 in FIG. 8; and) and that the permeability is far, far greater for the magnetic material (iron) than for air. Given a sufficient dimensioning of the iron paths, the entire magnetic potential difference then normally falls off in the air gap between magnet and armature. When the cross section of the iron return is reduced so far that the saturation induction of the return material is reached (e.g. at 13a, FIG. 3 without sleeve 10; and at 18, 18a, FIG. 7), then the magnetic flux is essentially limited by the cross section of the iron return. If the share of the leakage flux in the total flux is neglected, there approximately ensues the relationship $\phi \sim q_R$, whereby $q_R$ is the cross section of the saturated magnetically soft-iron return.

In the solution principle according to (2) above, one proceeds from the condition that the magnetic reluctances of the armature and of the low-retentivity magnetic return are negligibly small with respect to the air gap reluctances situated in the magnetic circuit (e.g. at 21, 21a, FIG. 9; and at 23, FIG. 13).

The equation $$\phi = \frac{H_m \cdot l_m}{\Sigma R_v}$$

is then valid for the flux $\phi$ in the magnetic circuit and, thus, $$\phi \sim (1/R_v).$$

Thereby, $H_m$ is the field strength in the magnet, $l_m$ is the length of the lines of flux in the magnet and $R_v$ is the sum of all air gap reluctances in the magnetic circuit. Thereby $$R_v = \frac{l_v}{\mu_o \cdot q_v}$$

The length of the lines of flux in the respective air gap is designated with $l_v$, $q_v$ is the effective air gap cross sectional area permeated by lines of flux, and $\mu_o$ is the permeability constant in air.

With the above relationships, there ensues a flux change with the change of the air gap length according to the relationship $$\phi \sim (1/l_v)$$

In the solution principle according to (3) above, one proceeds from the condition that the magnet flux in the armature depends on the flux of the magnet less the magnetic flux components in the shunt, namely according to the relationship $$\phi \text{ armature} = \phi \text{ magnet} - \phi \text{ shunt}.$$

The measure of the attainable field weakening is a function of the changable air gap length and of the part of the permanent magnet surface which is shunted.

With the solution possibilities revealed, the rpm can be reduced over a greater range (approximately by the factor 0.5 up to a maximum 0.3, i.e. a maximum reduction to thirty percent of the normal maximum speed range. In addition to this rough adjustment, the rpm can also be changed by means of the change of the armature voltage for a fine adjustment in a known manner.

It will be apparent that many modifications and variations may be effected without departing from the scope of the novel concepts and teachings of the present invention.

We claim as our invention:

1. A dental tool drive system comprising a d.c. subfractional horsepower motor with permanent-magnetic excitation and with rotor output means including an armature (11) for the drive of a tool rotatably seated in a dental hand instrument selectively over relatively high and relatively low dental speed ranges, said system further comprising a cylindrical motor housing (13') having permanent magnets (12, 12a) therein for the excitation of the armature (11) and arranged with poles lying diametrically opposite one another, said motor housing comprising a sleeve encircling the armature and forming a stationary return flux path and being of low retentivity material for this purpose, said sleeve having the permanent magnets (12, 12a) secured thereto so as to provide for an air gap between the permanent magnets (12, 12a) and the armature (11), a plurality of pole shoes (22, 22a) of low retentivity magnetic material corresponding to the plurality of said permanent magnets (12, 12a) and rotatably arranged concentrically thereto in the air gap between the armature (11) and permanent magnets; and manually operable dental speed range selector means coupled with the pole shoes (22, 22a) and comprising an actuation element (25) extending through the motor housing to the exterior thereof for manual actuation for the selection of the dental speed range of the dental hand instrument, and arranged for manual switchover to shift the pole shoes from a first work position (FIG. 12) increasing the magnetic flux through the armature to a maximum value for dental work into a second work position (FIG. 13) which decreases the magnetic flux to a minimum value, whereby depending upon the working position of said actuation element (25) adjustment of armature current selectively adjusts the speed of the dental tool over a minimum dental speed range and over a maximum dental speed range.

2. A dental tool drive system according to claim 1, with said dental speed range selector means comprising an end-face ring (24) of nonmagnetic material, the actuation element (25) being secured at the ring, said motor housing having an arcuate slot (26) receiving said actuation element (25) and providing for a limited angle of rotation of said actuation element (25) corresponding to the shifting of said pole shoes (22, 22a) between said first and second work positions.

Figure 12:
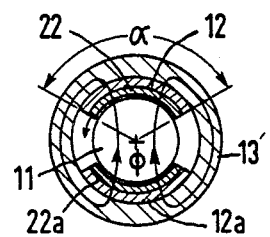

3. A dental tool drive system according to claim 2, with the permanent magnets (12, 12a) and pole shoes (22, 22a) each forming in cross section a section of an annulus, and the circumferential angular extent (α) of the pole shoes (22, 22a) being dimensioned in such manner that their ends are covered by the permanent magnets (12, 12a) in both work positions (FIGS. 12 and 13).

4. The method of operating a dental tool drive system in accordance with claim 15 which method comprises manually shifting the actuation element (25) to effect manual switchover of the pole shoes (22, 22a) between the first work position (FIG. 12) and the second work position (FIG. 13), and, depending upon the working position of the actuating element (25), adjusting the armature current supplied to said armature to selectively adjust the speed of the dental tool seated in the dental hand instrument over a minimum dental speed range and over a maximum dental speed range.

5. A dental tool drive system comprising a d.c. subfractional horsepower motor with permanent magnetic excitation and with rotor output means including an armature (11) for the drive of a tool rotatably seated in a dental hand instrument selectively over relatively high and relatively low dental speed ranges, said system further comprising a cylindrical motor housing having permanent magnets (12, 12a) therein for exciting the armature and arranged with poles lying diametrically opposite one another, said motor housing comprising a first sleeve (13) encircling the armature and having the permanent magnets (12, 12a) arranged therein, the first sleeve (13) being of low retentivity material with a relatively thin wall thickness and forming a stationary return flux path, a second means for fitting over the first sleeve (13), the second means forming a positionally changeable return flux path (10; 16, 16a) of low retentivity material with a significantly greater wall thickness in comparison to the first sleeve (13), the second means forming the locationally changeable return flux path being a component of a dental hand instrument (2) which can be releasably coupled to the rotor output means (5) of the motor (1), and the second means being dimensioned in such manner that it overlies the first sleeve (13) in the coupled state at least over a part of the length (L) of the permanent magnets (12, 12a).

6. A dental tool drive system according to claim 5, with the second means comprising a second sleeve (14) forming the locationally changeable return flux path, said sleeve having recesses (15) extending along the permanent magnets (12, 12a), which recesses subdivide the second sleeve as seen over the length (L) of the magnets (12, 12a) into two sections (16, 16a) representing in cross-section sectors of an annulus; the second sleeve (14) with the sections (16, 16a) being rotatably arranged around a centrical axis (M) with respect to the permanent magnets (12, 12a).

7. A dental tool drive system according to claim 6, with the circumferential angular extent (α) for the permanent magnets (12, 12a) and the sections (16, 16a) being dimensioned in such manner that the sections (16, 16a), at their ends cover the pole ends of the magnets (12, 12a).

8. A dental tool drive system according to claim 7, with the sections (16, 16a) and the permanent magnets (12, 12a) having a circumferential angular extent of one hundred and twenty angular degrees (α = 120°).

9. The method of operating a dental tool drive system according to claim 5 which comprises selectively applying to the dental hand instrument a second sleeve (10) so that the second sleeve can be slipped over the first sleeve (13) so as to overlie the first sleeve (13) in the coupled state of the rotor output means (5) with the tool rotatably seated in the dental hand instrument for the drive of the tool over said relatively low dental speed range.

10. The method of operating a dental tool drive system in accordance with claim 6 which comprises providing a second sleeve (14) having recesses (15) as a component of the dental hand instrument (2) with the rotor output means (5) coupled with the tool of said dental hand instrument, selectively rotating said second sleeve (14) between respective extreme angular positions representing a first work position (FIG. 5) which increases the magnet flux through the armature to a maximum value for dental work into a second work position (FIG. 6) which decreases the magnetic flux to a minimum value for dental work, and, depending upon the working position, adjusting the armature current supplied to said armature to selectively adjust the speed of the dental tool seated in the dental hand instrument over a minimum dental speed range and over a maximum dental speed range.

* * * * *